US006982028B2

(12) United States Patent
Johnson et al.

(10) Patent No.: US 6,982,028 B2
(45) Date of Patent: Jan. 3, 2006

(54) SURFACE CHARGE MODIFICATION WITHIN PREFORMED POLYMER MICROCHANNELS WITH MULTIPLE APPLICATIONS INCLUDING MODULATING ELECTROOSMOTIC FLOW AND CREATING MICROARRAYS

(75) Inventors: Timothy J. Johnson, Gaithersburg, MD (US); Emanuel A. Waddell, Jr., Gaithersburg, MD (US); David J. Ross, Gaithersburg, MD (US); Laurie E. Locascio, North Potomac, MD (US)

(73) Assignee: The United States of America as represented by the Secretary of Commerce, Washington, DC (US)

( * ) Notice: Subject to any disclaimer, the term of this patent is extended or adjusted under 35 U.S.C. 154(b) by 504 days.

(21) Appl. No.: 09/905,566

(22) Filed: Jul. 13, 2001

(65) Prior Publication Data

US 2002/0023840 A1 Feb. 28, 2002

Related U.S. Application Data

(60) Provisional application No. 60/260,577, filed on Jan. 9, 2001.

(51) Int. Cl.
*B01D 61/42* (2006.01)
*C02F 1/469* (2006.01)

(52) U.S. Cl. .................. 204/454; 204/600; 204/601; 204/602; 204/450; 204/451
(58) Field of Classification Search ............... 204/454, 204/451, 450, 600, 601, 602
See application file for complete search history.

(56) References Cited

PUBLICATIONS

Locascio et al., "Measurement of electroosmotic flow in plastic imprinted microfluid devices and the effect of protein adsorption on flow rate", Journal of Chromatography A, 857, 275–284(1999).*

* cited by examiner

*Primary Examiner*—Ling-Sui Choi
(74) *Attorney, Agent, or Firm*—Butzel Long

(57) ABSTRACT

A method is described for modifying performed channels fabricated in a variety of substrate materials including PMMA. The method involves exposing a portion of a fluid flow channel to light at a fluence and wavelength which modifies the surface charge of the substrate at the exposure site. The method can be used to modulate electroosmotic flow in channels or to immobilize chemical compounds or biological species in the fluid flow channels at the modified surfaces. The method can be used to fabricate or modify microfluidic systems

25 Claims, 9 Drawing Sheets

SURFACE CHARGE MODIFICATION WITHIN PREFORMED POLYMER MICROCHANNELS WITH MULTIPLE APPLICATIONS INCLUDING MODULATING ELECTROOSMOTIC FLOW AND CREATING MICROARRAYS

RELATED APPLICATION

This application is based on United States Provisional Patent Application Ser. No. 60/260,577 filed Jan. 9, 2001, the complete disclosure of which is expressly incorporated herein by reference.

TECHNICAL FIELD

The present invention relates to micro-total-analytical systems having fluid flow channels. More particularly, the present invention is directed to methods to modify and control fluid flow in micro-total-analytical systems and to immobilize chemical components and species thereon, and to micro-total-analytical systems which have been treated according to the techniques of the present invention.

BACKGROUND ART

Over the past decade there has been a significant focus of research on the development of micro-total-analytical systems which are referred to as μ-TAS or lab-on-a-chip devices. This technology is based on the use of a series of microfluidic channels or microchannels for the movement, separation, reaction, and/or detection of various chemicals (e.g. proteins, DNA, chemical compounds, etc.). Movement of the fluids within the microchannels can be effected by means of applied pressure gradients or electric fields applied along the length of the channel. In the latter phenomenon, known as electroosmosis, the larger the magnitude of the applied electric field or the greater the surface charge, the greater the induced fluid velocity.

The development of lab-on-a-chip devices has progressed rapidly, however there are still several issues that must be resolved. Most of these issues stem from the need to control flow and/or immobilize reagents within the fluid flow channels. Such control or immobilization can be achieved through the modification of the surface charges. Since electroosmotic flow is a result of surface charge, the ability to change the charge is critical to the optimization of lab-on-a-chip devices. One method for controlling and changing the surface charge is through the use of wall coatings, which has been shown to increase, decrease, or even reverse the electroosmotic flow in specific regions of the channels. Unfortunately, the use of wall coatings complicates and increases the costs of the fabrication process. Moreover, such coatings may become unstable over time.

Surface charge modification of the microchannels is also used to selectively bind molecules such as DNA, proteins, molecules, etc. therein. Such bound molecules can then be used in devices that function as chemical sensors, DNA or protein microarrays, etc. Current reported methods for binding proteins require a rather complex soft lithography technique. Another process uses a two-step lamination technique or a two-step bovine serum albumin (BSA) blocking technique to pattern proteins. These procedures tend to complicate the fabrication process.

DISCLOSURE OF THE INVENTION

According to various features, characteristics and embodiments of the present invention which will become apparent as the description thereof proceeds, the present invention provides a method of modifying fluid flow in a channel formed in a polymeric substrate which involves:

exposing a portion of the channel to laser light at a fluence and wavelength(s) which are sufficient to change a surface charge at the exposed portion of the channel.

The present invention also provides a method of immobilizing a chemical species in a channel formed in a polymeric substrate which involves:

exposing a portion of the channel to laser light at a fluence and wavelength(s) which are sufficient to ablate and/or change a surface charge at the exposed portion of the channel.

The present invention further provides a micro-total-analytical system having a polymeric substrate with a fluid flow channel, wherein a portion of the fluid flow channel which has been surface-charged modified by exposure to laser light.

BRIEF DESCRIPTION OF DRAWINGS

The present invention will be described with reference to the attached drawings which are given as non-limiting examples only, in which.

BEST MODE FOR CARRYING OUT THE INVENTION

The present invention is directed to a simple fabrication method to modulate the surface charge of a solid substrate. The present invention is based upon the discovery that the surface charge of a polymeric substrate, such as a poly (methyl methacrylate) (PMMA) substrate, a polycarbonate substrate, a poly(ethylene terephthalate glycol) substrate, etc., can be modified by exposing the surface to a light source that will chemically modify and/or ablate the surface. Moreover, the amount of surface charge created depends on a number of factors including, the substrate material, the wavelength of the light source, the fluence (defined as the light power divided by the exposure area), the exposure time, the number of times that the same surface is exposed to the light source, and the local process environment.

During the course of the present invention, a laser was used to chemically modify a surface of a pre-formed channel in a polymeric substrate. Such chemical modification of the surface was found to effect fluid flow control and/or immobilization of various chemicals and chemical species due to modification of the surface charges. Effective fluid flow control has been verified from electrokinetic flow profile studies comparing flow in modified and non-modified, pre-formed microchannels.

The principles of the present invention have been applied to simple, one-step processes with ultraviolet (UV) laser pulses for patterning proteins (or other charged entities) in a linear or two-dimensional microarray pattern within pre-formed microfluidic channels. For the flow modification studies, the fluence level of the UV laser was adjusted so that there was no physical or structural changes to the channel, but so that there was a change in the surface charge on the UV-exposed surface as evidenced by the increase in fluid velocity over that surface.

Figure 1A:
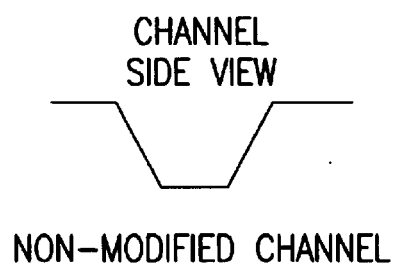
FIG. 1a is a schematic of a non-modified imprinted channel with a depiction of the electroosmotic flow profile.
Figure 1B:
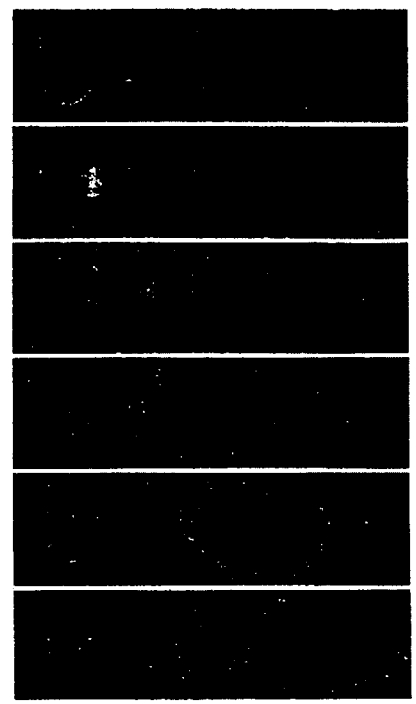
FIG. 1b is a top view of a time series of images of electroosmotic flow profiles within a non-modified imprinted channel.
Figure 1C:
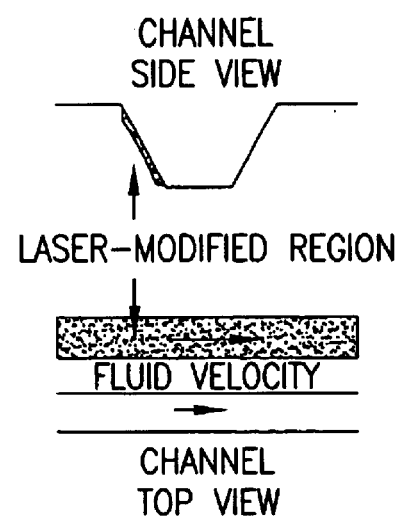
FIG. 1c is a schematic of a UV-modified imprinted channel with a depiction of the electroosmotic flow profile.
Figure 1D:
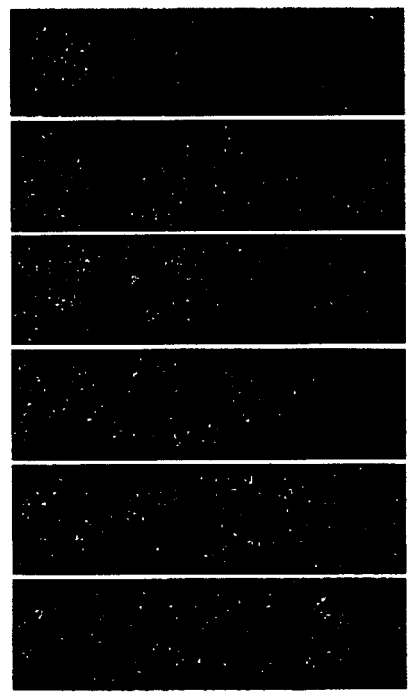
FIG. 1d is a top view of a time series of images of electroosmotic flow profiles within a UV-modified imprinted channel.

FIGS. 1a and 1b are schematic drawings and captured top-view images of electroosmotic flow profiles within a non-modified, imprinted channel as observed by fluorescence microscopy, respectively. The electric field strength used in FIG. 1b was 266 V/cm and the time step between images was 67 ms. FIGS. 1c and 1d are schematic drawings and captured top-view images of electroosmotic flow profiles within a UV-modified, imprinted channel as observed by fluorescence microscopy, respectively. The electric field strength used in FIG. 1d was 244 V/cm and the time step between images was 67 ms. It can be seen in FIG. 1d that the fluid at the top of the channel is moving faster than the fluid at the bottom due to the increase in charge on the UV-modified surface.

Figure 2A:
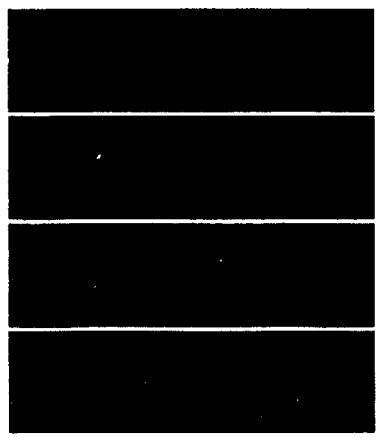
FIGS. 2a and 2b are top views of electroosmotic flow profiles for a UV-laser-modified surface within an imprinted channel at an applied electric field of 488 V/cm (FIG. 2a), and of 732 V/cm (FIG. 2b).
Figure 2B:
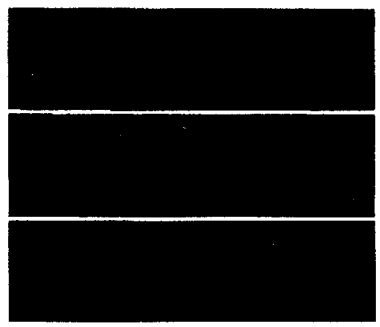

The lack of ablation upon exposure to the UV light is referred to as subablation. The effect of the laser-modified surface on the electroosmotic flow profile is evidenced more clearly at higher electric field strengths, as shown in FIGS. 2a and 2b. FIGS. 2a and 2b are top views of electroosmotic flow profiles as observed by fluorescence microscopy for a UV-laser-modified surface within the pre-formed, imprinted channel, and an applied electric field of 488 V/cm (FIG. 2a), and 732 V/cm (FIG. 2b). The time step between images was 50 ms.

The surface-charge modification of pre-formed microchannels can also be used to selectively bind biological species or other chemical compounds.

Figure 3A:
FIGS. 3a and 3b are top views of a trapezoidally-shaped, imprinted microchannel with a linear array of ablated spots for the binding of fluorescein-labeled BSA imaged using white light microscopy (FIG. 3a), and fluorescence microscopy (FIG. 3b).
Figure 3B:

FIGS. 3a and 3b are top views of a trapezoidally-shaped microchannels with a linear array of ablated spots for the binding of fluorescein isothiocyanate (FITC) labeled BSA imaged using white light microscopy (FIG. 3a), and fluorescence microscopy (FIG. 3b). The fluorescence in FIG. 3b shows selective binding of BSA to the ablated spots compared to the surrounding, non-irradiated surface.

Figure 4A:
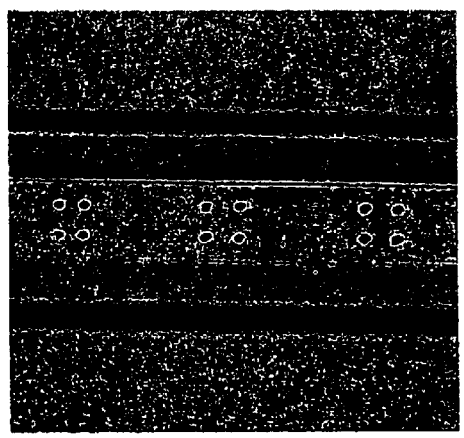
FIGS. 4a and 4b are top views of a trapezoidally-shaped microchannel with a 2D array of ablated spots for the binding of fluorescein-labeled BSA imaged using white light microscopy (FIG. 4a), and fluorescence microscopy (FIG. 4b).
Figure 4B:
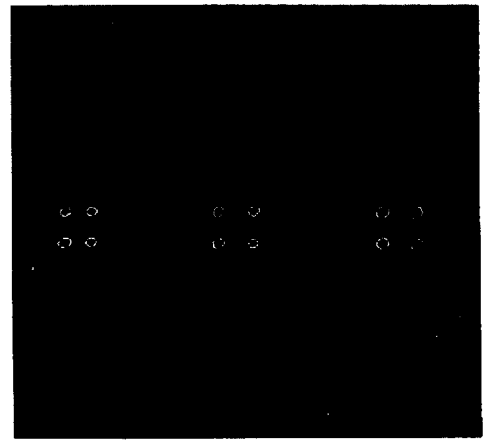

FIGS. 4a and 4b are top views of a trapezoidally-shaped microchannel with a two-dimensional array of ablated spots for the binding of FITC-labeled BSA imaged using white light microscopy (FIG. 4a), and fluorescence microscopy (FIG. 4b)

The higher fluences were used to ablate material to create an increase in surface charge and surface area for the selective binding of proteins without the use of laminate or other blocking techniques.

The technique of using a laser to create an increase in the surface charge of a solid substrate is not limited to ablation level fluences for micoarrays or subablation level fluences for electroosmotic flow modifications. Ablation level fluences create a higher surface charge than subablated surfaces. Also, ablated surface can have a higher surface area compared to native or subablated surfaces. Therefore, it is to be understood that application of the techniques of the present invention provide benefits from ablation level fluences for some purpose and subablation level fluences for other purposes.

Furthermore, it is to be understood that the application of this technique is not limited to the use of a laser but to any light source of sufficient energy to induce a chemical modification of the surface.

In the following illustrative examples, experiments were conducted to demonstrate the ability to modify the surface charge on a polymeric substrate. For illustrative purposes a poly(methyl methacrylate) (PMMA) substrate was used in the following examples. Inasmuch as the examples are merely illustrative, it is to be understood that the techniques of the present invention are not limited to the specific polymeric substrates or wavelengths of lights of light used in the examples.

In the following examples a poly(methyl methacrylate) (PMMA) substrate was provide with channels formed by an imprinting method. Prior to imprinting, the PMMA substrate was cleaned with compressed air. Channels were imprinted in the substrate material using a silicon stamp with a trapezoidal-shaped raised channel. It is to be understood that a polymeric substrate having channels made utilizing techniques other than imprinting, including for example injection molding, embossing, lithography, machining, etc. could also be used according to the present invention.

Figure 5:
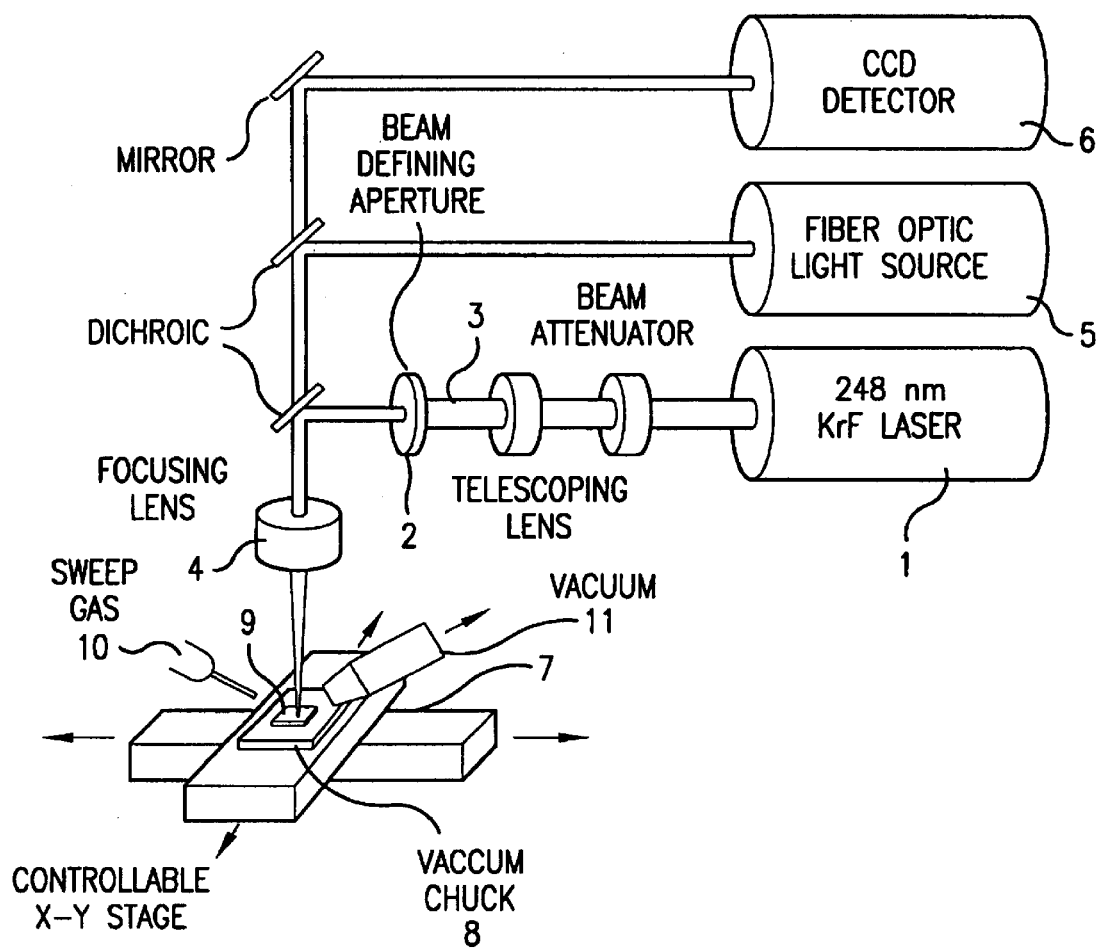
FIG. 5 is a schematic diagram of a UV-laser system used to modify polymer microchannels according to one embodiment of the present invention.
Figure 6A:
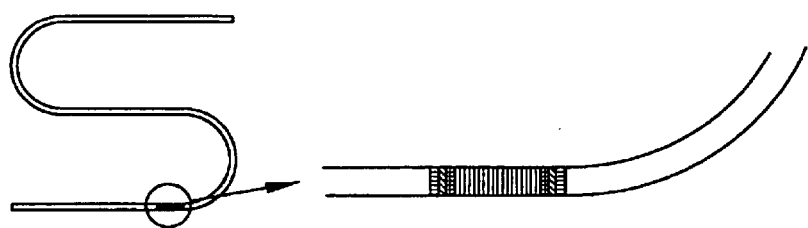
FIGS. 6a–6e are progressive views of electroosmotic flow of a sample plug through a typical non-modified S-shaped microchannel.
Figure 6B:
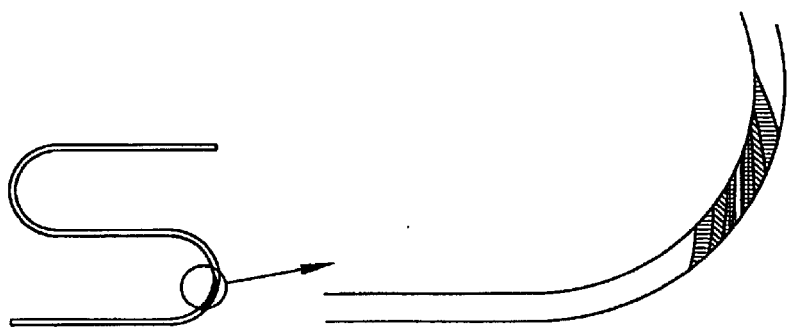
Figure 6C:
Figure 6D:
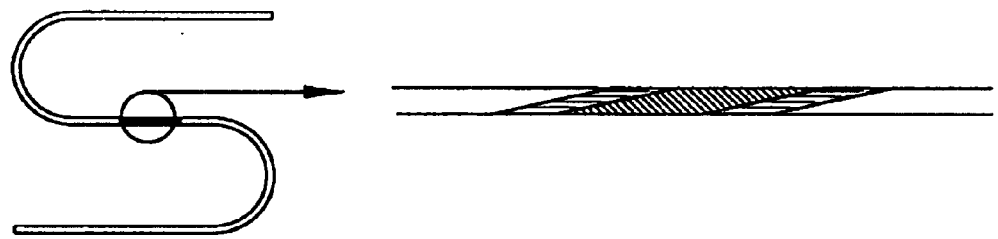
Figure 6E:
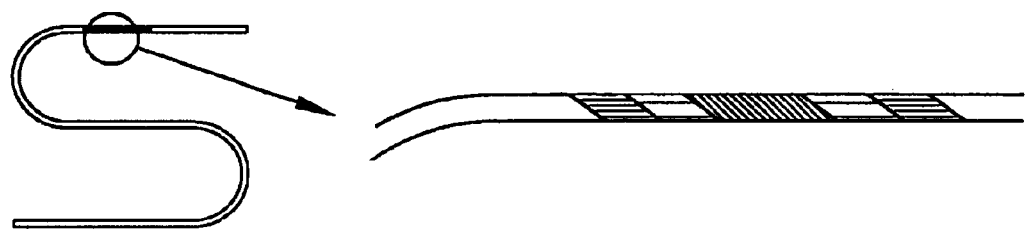
Figure 7A:
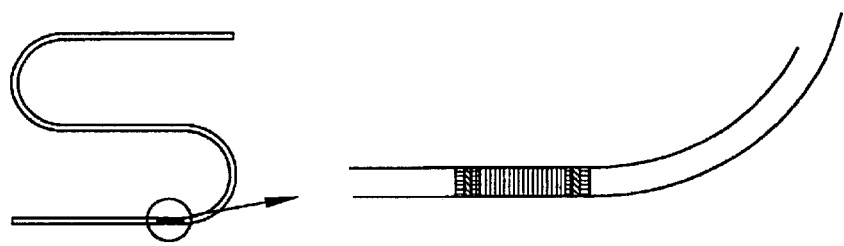
FIGS. 7a–7e are progressive views which illustrate electroosmotic flow of a sample plug in an S-shaped microchannel in which the outer wall of each non-linear region has been surface charge modified according to the present invention.
Figure 7B:
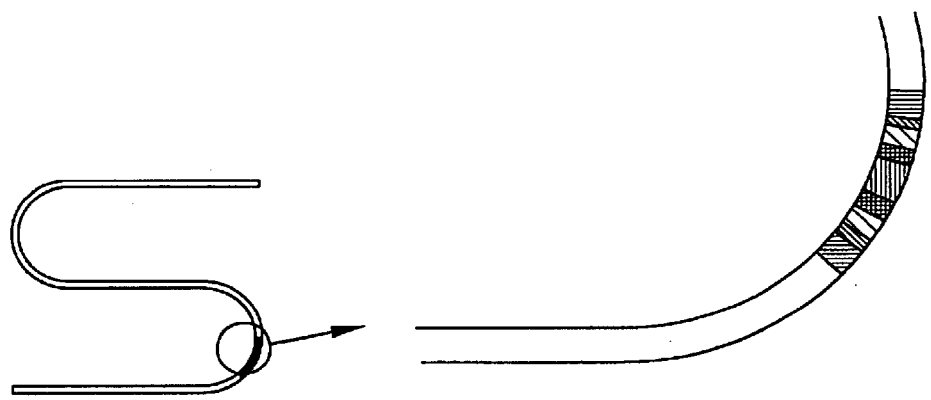
Figure 7C:
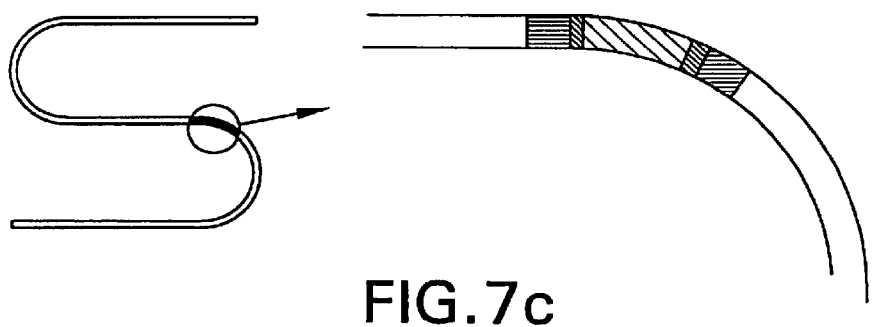
Figure 7D:
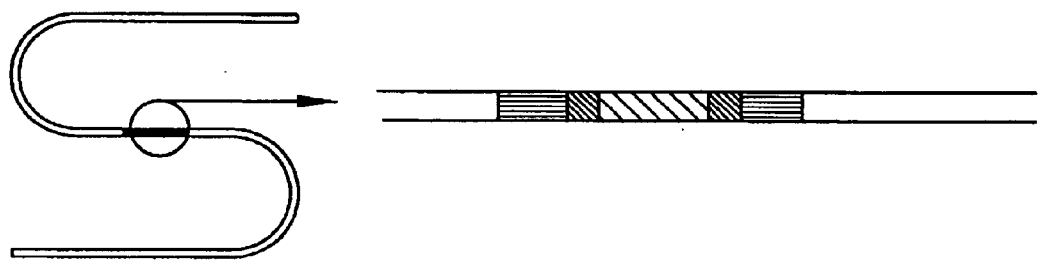
Figure 7E:
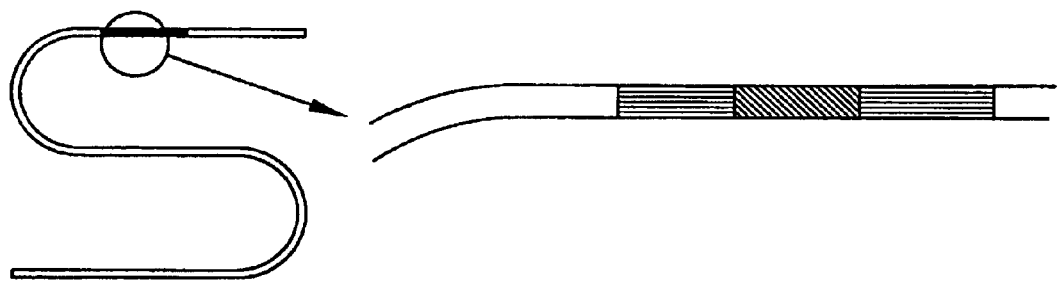

FIG. 5 is a schematic diagram of a UV-laser system used to modify polymer microchannels according to one embodiment/of the present invention. The excimer laser system (LMT-4000, Potomac Photonics, Inc., Lanham, Md.) of FIG. 5 was used to surface-modify PMMA substrates at fluences below, the ablation threshold so that, although no change in the physical dimensions of the substrate occurred, a change in the surface charge of the exposed surface did occur. If ablation of the substrate surface is not a concern, the surface can be modified at higher fluences, with an even greater effect on surface charge, but a change in physical dimensions and characteristics of the channel will occur. The system depicted in FIG. 5 contains a laser light source 1, an aperture 2 for delimiting the size and shape of the beam 3, a focusing lens 4, a visible light source 5, a CCD camera 6 to image the ablation process, and a controllable X–Y stage 7 with a vacuum chuck 8 to hold the substrate 9 in place. Also, a nozzle 10 is present to sweep gas over the substrate 9 during processing, and a vacuum 11 is located on the opposite side to remove debris.

EXAMPLE 1

In this example the UV-laser system depicted in FIG. 5 was used to modify the surfaces of imprinted channels in a PMMA substrate (discussed above) for electroosmotic flow modification. First, the PMMA substrate with the preformed imprinted channels was placed on the vacuum chuck 8 and a vacuum was applied to keep the PMMA substrate stationary. A beam-defining aperture 2 was chosen so that the light, after being focused, exposed a square area of $1.70 \times 10^{-5}$ cm$^2$ on the surface of the PMMA substrate. Other exposure areas can be used depending on what is desired. The power level per pulse was set to an average of 6.4 µJ, and the frequency of pulses was set to 200 Hz (pulse duration of 7 ns). Nitrogen was used as the sweep gas, and the laser was exposed to a single surface of the microchannel as the stage moved at a rate of 1 mm/sec in one direction. Other operating parameters can be used depending on what is desired.

EXAMPLE 2

In this example, the UV-laser system depicted in FIG. 5 was used to create ablated spots on the bottom of an imprinted channel. First, the PMMA with the preformed imprinted channel (discussed above) was placed on the vacuum chuck 8 and a vacuum was applied to keep the PMMA substrate stationary. A beam-defining aperture 2 was chosen such that the light, after being focused, exposed a circular area of $2.2 \times 10^{-7}$ cm$^2$ for a linear array or $9.1 \times 10^{-8}$ cm$^2$ for two-dimensional microarrays on the surface of the PMMA substrate. The power level per pulse was set to an average of 1.48 µJ for the linear arrays and 0.182 µJ for the two-dimensional microarrays. The frequency of pulses was set to 200 Hz with an average pulse duration of 7 ns. Nitrogen was swept over the surface during UV-light exposure. After ablating the spots, the PMMA substrate was sonicated for 10 minutes in a water solution to remove any weakly bounded particulates that were generated during the ablation process. Other light exposure areas and other operating parameters can be used depending on what is desired.

EXAMPLE 3

In this example, the imprinted and laser modified microchannel in the PMMA substrate from Examples 1 was covered and sealed with an additional sheet of PMMA which is referred to herein as the "lid." Circular holes having a diameter of 3 mm were formed in the lid to provide access to the underlying channel(s). The holes also served as fluid reservoirs. In order to seal the microchannel, the lid was placed on top of the channel and the two pieces were clamped together between glass slides and bonded by placing them in a circulating air oven at 103° C. for 12 minutes. The channels were 2–5 cm in length and 30 µm deep. The channels had a trapezoidal cross section defined by the silicon template with a 25 µm width at the bottom and a 70 µm width at the top.

EXAMPLE 4

In this example, fluorescein isothiocyanate labeled Bovine Serum Albumin (FITC-BSA) was immobilized at the ablated spots on the bottom of an imprinted channel from Example 2. The FITC-BSA was obtained from Sigma-Aldrich (St. Louis, Mo.) and was concentrated to 1 mg/ml in a phosphate buffered saline (PBS) solution. The channel was submerged in the FTIC-BSA solution for varying times ranging from 30 mins to 17 h. Afterwards, the substrate was rinsed three times under agitation with PBS. A drop of the PBS was then placed over the channel and then covered with a coverslip for observation by microscopy.

As noted above, FIGS. 1–3 illustrate how the techniques presented in the Examples control fluid flow and immobilization of chemical species.

The present invention has many practical applications. For example, the principles of the present invention can be used to modify electroosmotic flow and eliminate band broadening due to microchannel turns.

As microfluidic devices increase in complexity due to the integration of various physical manipulations and chemical reactions, a corresponding increase in the number, and complexity, of microchannels on a single microchip will take place. This increase in complexity will often lead to the incorporation of various turns in the microchannel design. This is especially true for microchannels that are responsible for the separation of chemical species because these channels often require the greatest channel length. Unfortunately, the introduction of turns leads to analyte dispersion due to the difference in length scales between the inside and the outside of the turn. This is known as the racetrack effect because the fluid on the inside of the turn will complete the turn sooner than the fluid on the outside due to the shorter distance. Furthermore, for electrokinetic flow, the strength of the applied electric field is greater on the inside of the turn than on the outside of the turn. Therefore the fluid on the inside of the turn will travel faster than fluid on the outside of the turn.

FIGS. 6a–6e are progressive views which depict electroosmotic flow of a sample plug in a non-modified, S-shaped microchannel. The analyte dispersion or racetrack effect depicted in FIGS. 6a–6e is due to the nonuniform electric field in the curved microchannel as well as the differences in length scales between the inside and outside of the turn. These factors lead to analyte dispersion as shown in FIGS. 6a–6e. Thus, when turns are introduced into a separation channel (or any other channel), analyte dispersion will occur. This effect leads to a reduction in the separation efficiency of the channel and inhibits the reduction of the overall lab-on-a-chip size.

The present invention will help (1) reduce or eliminate analyte dispersion for electrokinetic flow through curved or non-linear microchannels, (2) maintain a geometrically simple microchannel curve, and (3) reduce the expense and the complexity of microchannel fabrication. For example, the entire curved microchannel can be formed using any suitable technique such as an imprint technique, an injection molding technique, etc., and then the outside of the already formed curve can be exposed to light according to the present invention to increase the surface charge on the outside surface. Thus, the outside of the analyte plug will increase in speed to keep up with the fluid on the inside of the curve, thereby reducing plug dispersion.

FIGS. 7a–7e are progressive views which illustrate electroosmotic flow of a sample plug in an S-shaped microchannel which has been surface-charge modified according to the present invention. The plug remains uniform due to surface-charge modification of the outside of each turn of the channel.

Figure 8A:
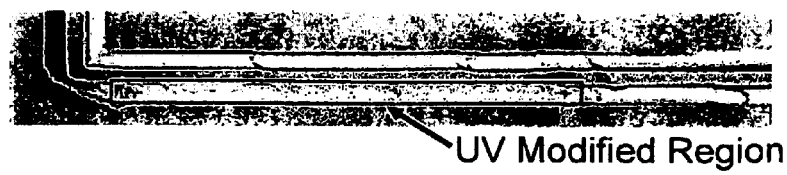
FIG. 8a is a top-view image of a trapezoidal-shaped, imprinted channel with a 90 degree turn.
Figure 8B:
FIGS. 8b and 8c are a time series of images of a fluorescein plug of fluid undergoing electroosmotic flow in a non-modified, imprinted channel with a 90 degree turn and a UV-modified, imprinted channel with a 90 degree turn, respectively. The outer wall of the imprinted channel in FIG. 8c has been surface charge modified according to the present invention.
Figure 8C:

FIGS. 8a is a top-view image of a trapezoidal-shaped, imprinted channel with a 90 degree turn as viewed by white-light microscopy. FIGS. 8b and 8c are a time series of images of a fluorescein plug of fluid undergoing electroosmotic flow as viewed by fluorescence microscopy. FIG. 8b is flow in a non-modified, imprinted channel with a 90 degree turn, at an applied electric field of 454 V/cm, and imaged at time points of 0, 83, and 417 ms. FIG. 8c is flow in a UV-modified, imprinted channel with a 90 degree turn, at an electric field 476 V/cm, and imaged at time points of 0, 67, and 333 ms. The outer wall of the imprinted channel in FIG. 8c has been surface charge modified over a length of 500 $\mu$m (as shown in FIG. 8a) according to the present invention, which results in a final plug that is more compact (FIG. 8c) compared to the extent of plug-broadening in the non-modified channel (FIG. 8b).

The principles of the present invention can also be used to provide a simple, one-step technique for selectively binding various chemicals and chemical species in predefined patterns. For example, biological species such as DNA, proteins, and/or other chemical compounds or species can be bound or immobilized within a pre-formed microchannel. Such binding or immobilization can be achieved by producing highly charged spots using the laser techniques described above, and then selectively immobilizing (either covalently or non-covalently) one or more types of chemicals or biological species. Such microchannel arrays can be used for the purpose of drug discovery, chemical sensing and similar or related applications.

The principles of the present invention can be used in conjunction with chemical means for modifying the surface charge of a substrate. For example, modulation of the surface charge of a substrate by chemical derivatization (e.g. wall coatings; etc.) can be conducted after the surface is modified by laser treatment according to the present invention. In such instances, an increase in the surface charge of laser-modified regions leads to an increase in surface reactivity for further chemical derivatization.

It has also been found that the laser treatment used to modify the surface change according to the present invention can also be used to modulate mechanical or electrokinetic fluid flow by altering the wetting properties, i.e. hydrophobicity/hydrophilicity, of a surface. For example, hydrophobic patches produced in a hydrophilic microchannel utilizing the laser surface-charge modification techniques of the present invention can hinder or stop flow thereby acting as a passive valve for microsystems.

Figures 9A, 9B, 9C:
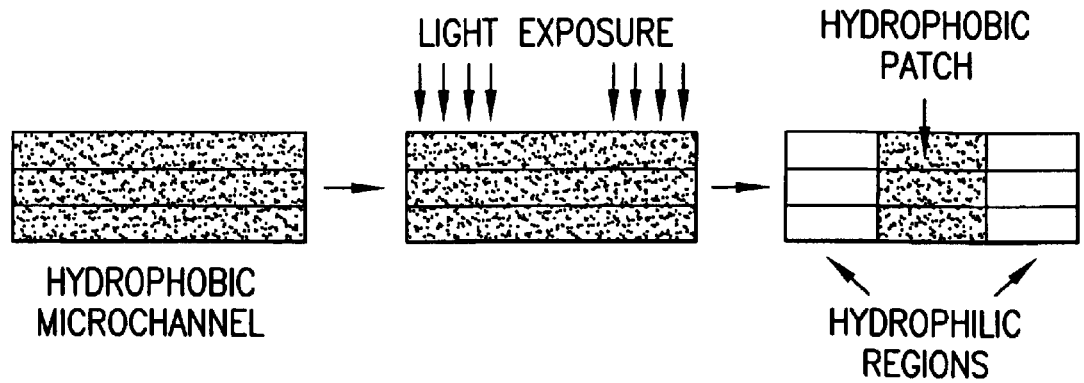
FIGS. 9a–9c depict how laser modification can create hydrophilic/hydrophobic regions within a preferred hydrophobic microchannel.

FIGS. 9a–9c show how laser modifications create hydrophilic/hydrophobic regions within a pre-formed hydrophobic microchannel. FIG. 9a illustrates a hydrophobic microchannel. FIG. 9b depicts how laser light is selectively directed onto portions of the hydrophobic microchannel. FIG. 9c depicts how the laser-exposed areas become hydrophilic while the unexposed areas remain hydrophobic.

Although the present invention has been described with reference to particular means, materials and embodiments, from the foregoing description, one skilled in the art can easily ascertain the essential characteristics of the present invention and various changes and modifications can be made to adapt the various uses and characteristics without departing from the spirit and scope of the present invention as described in the attached claims.

What is claimed is:

1. A method of modifying fluid flow in a channel formed in a substrate which comprises: exposing only one or more discrete, isolated portions of the channel to light at a fluence which is sufficient to change a surface charge at the one or more discrete, isolated exposed portions of the channel.

2. A method of modifying fluid flow in a channel formed in a substrate according to claim 1, wherein the one or more discrete, isolated portions of the channel is exposed to light at a fluence and wavelength(s) which are sufficient to alter the surface charge at the exposed portion of the channel, and wherein the substrate is not ablated by the light.

3. A method of modifying fluid flow in a channel formed in a substrate according to claim 1, wherein the fluence causes ablation of the substrate.

4. A method of modifying fluid flow in a channel formed in a substrate according to claim 3, wherein the one or more discrete, isolated portions of the channel which is exposed to light comprises at least one of a wall of the channel, a bottom of the channel, and one or more portions thereof.

5. A method of modifying fluid flow in a channel formed in a substrate according to claim 3, wherein the channel is linear.

6. A method of modifying fluid flow in a channel formed in a substrate according to claim 3, wherein the channel is non-linear.

7. A method of modifying fluid flow in a channel formed in a substrate according to claim 3, wherein the one or more discrete, isolated portions of the channel is exposed to at least one of a linear and non-linear pattern of light.

8. A method of modifying fluid flow in a channel formed in a substrate according to claim 3, wherein the substrate is a member selected from the group consisting of polymeric, glass, silica, ceramic, and composites thereof.

9. A method modifying fluid flow in a channel formed in a polymeric substrate according to claim 3, wherein the substrate is selected from the group consisting of a poly (methyl methacrylate) substrate, a polycarbonate substrate, a poly(ethylene terephthalate glycol) substrate, a polystyrene substrate, and a poly(vinyl chloride) substrate.

10. A method of modifying fluid flow in a channel formed in a substrate according to claim 3, wherein the substrate comprises a microfluidic system.

11. A method of modifying fluid flow in a channel formed in a substrate according to claim 2, wherein the one or more discrete, isolated portions of the channel which is exposed to light comprises at least one of a wall of the channel, a top of the channel, a bottom of the channel, and portions thereof.

12. A method of modifying fluid flow in a channel formed in a substrate according to claim 3, wherein the channel is linear.

13. A method of modifying fluid flow in a channel formed in a substrate according to claim 3, wherein the channel is non-linear.

14. A method of modifying fluid flow in a channel formed in a substrate according to claim 3, wherein the portion of the channel is exposed to at least one of a linear and non-linear pattern of light.

15. A method of modifying fluid flow in a channel formed in a substrate according to claim 3, wherein the substrate is a member selected from the group consisting of polymeric, glass, silica, ceramic, or composites thereof.

16. A method of modifying fluid flow in a channel formed in a polymeric substrate according to claim 3, wherein the substrate is selected from the group consisting of a poly (methyl methacrylate) substrate, a polycarbonate substrate, a poly(ethylene terephthalate glycol) substrate, a polystyrene substrate, and a poly(vinyl chloride) substrate.

17. A method of modifying fluid flow in a channel formed in a substrate according to claim 3, wherein the substrate comprises a microfluidic system.

18. A method of immobilizing a chemical species in a channel formed in a substrate which comprises: exposing the one or more discrete, isolated portions of the channel to light at a fluence which is sufficient to change a surface charge at the exposed portion of the channel; and applying a chemical species to the exposed portion of the channel.

19. A method of immobilizing a chemical species in a channel formed in a substrate according to claim 18, wherein the chemical species comprises a chemical compound.

20. A method of immobilizing a chemical species in a channel formed in a substrate according to claim 18, wherein the chemical species comprises a biological species.

21. A method of immobilizing a chemical species in a channel formed in a substrate according to claim 18, wherein the one or more discrete, isolated portions of the channel that is exposed to the light comprises at least one of a wall of the channel, a bottom of the channel, and portions thereof.

22. A method of immobilizing a chemical species in a channel formed in a substrate according to claim 18, wherein the substrate is a member selected from the group consisting of polymeric, glass, silica, ceramic, or composites thereof.

23. A method of immobilizing a chemical species in a channel formed in a polymeric substrate according to claim 22, wherein the substrate is selected from the group consisting of a poly(methyl methacrylate) substrate, a polycarbonate substrate, a poly(ethylene terephthalate glycol) substrate, a polystyrene substrate, and a poly(vinyl chloride) substrate.

24. A method of immobilizing a chemical species in a channel formed in a substrate according to claim 18, wherein the substrate comprises a microfluidic system.

25. A method for immobilizing a chemical species in a channel formed in a substrate according to claim 24, wherein a microarray is formed in the microfluidic system.

* * * * *